United States Patent
Haubs et al.

(10) Patent No.: US 9,604,956 B2
(45) Date of Patent: *Mar. 28, 2017

(54) PROCESS FOR THE PRODUCTION OF TRIOXANE

(71) Applicant: Ticona GMBH, Sulzbach (Taunus) (DE)

(72) Inventors: Michael Haubs, Bad Kreuznach (DE); Klaus Kurz, Kelsterbach (DE); Jurgen Lingnau, Mainz-Laubenheim (DE)

(73) Assignee: Celanese Sales Germany GmbH, Sulzbach (Taunus) (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/359,319

(22) PCT Filed: Nov. 23, 2012

(86) PCT No.: PCT/EP2012/073539
§ 371 (c)(1),
(2) Date: May 20, 2014

(87) PCT Pub. No.: WO2013/076286
PCT Pub. Date: May 30, 2013

(65) Prior Publication Data
US 2014/0316147 A1    Oct. 23, 2014

(30) Foreign Application Priority Data

Nov. 24, 2011 (EP) .................................. 11190567
Nov. 24, 2011 (EP) .................................. 11190574
Nov. 24, 2011 (EP) .................................. 11190586

(51) Int. Cl.
| | |
|---|---|
| C07D 323/06 | (2006.01) |
| C07C 47/04 | (2006.01) |
| C08G 2/10 | (2006.01) |
| C08G 2/30 | (2006.01) |
| C08G 65/30 | (2006.01) |
| C08G 65/06 | (2006.01) |
| C08G 65/16 | (2006.01) |
| C08J 11/28 | (2006.01) |
| C08G 2/36 | (2006.01) |
| C07D 323/04 | (2006.01) |
| C08J 11/16 | (2006.01) |

(52) U.S. Cl.
CPC ............ *C07D 323/06* (2013.01); *C07C 47/04* (2013.01); *C07D 323/04* (2013.01); *C08G 2/10* (2013.01); *C08G 2/36* (2013.01); *C08G 65/06* (2013.01); *C08G 65/16* (2013.01); *C08G 65/30* (2013.01); *C08J 11/16* (2013.01); *C08J 11/28* (2013.01); *C08G 2650/62* (2013.01); *C08J 2359/02* (2013.01); *Y02P 20/125* (2015.11)

(58) Field of Classification Search
CPC ........ C07D 323/06; C07C 47/04; C08G 2/10; C08G 2/30; C08G 65/30; C08G 65/06; C08G 65/16; C08J 11/28

See application file for complete search history.

(56) References Cited

U.S. PATENT DOCUMENTS

| | | |
|---|---|---|
| 3,305,529 A | 2/1967 | Reynolds et al. |
| 3,457,227 A | 7/1969 | Kennedy |
| 3,471,998 A | 10/1969 | Ishida et al. |
| 3,506,615 A | 4/1970 | Chen |
| 3,697,546 A | 10/1972 | Asakawa et al. |
| 3,804,808 A | 4/1974 | Ishii et al. |
| 4,323,502 A | 4/1982 | Muck et al. |
| 4,330,474 A | 5/1982 | Nehring |
| 4,358,623 A | 11/1982 | Murphy et al. |
| 4,420,641 A | 12/1983 | Gerberich et al. |
| 4,450,301 A | 5/1984 | McMillan et al. |
| 4,563,536 A | 1/1986 | Yoshida et al. |
| 4,962,235 A | 10/1990 | Morishita et al. |
| 4,967,014 A | 10/1990 | Masamoto et al. |
| 5,008,463 A | 4/1991 | Beck et al. |
| 5,508,448 A | 4/1996 | Emig et al. |
| 5,767,294 A | 6/1998 | Steele et al. |
| 5,929,257 A | 7/1999 | Kashihara et al. |
| 6,232,507 B1 | 5/2001 | Kaiser et al. |
| 6,362,305 B1 | 3/2002 | Schweers et al. |
| 6,388,102 B2 | 5/2002 | Schweers et al. |
| 6,448,448 B1 | 9/2002 | Schweers et al. |
| 6,472,566 B2 | 10/2002 | Schweers et al. |
| 6,653,487 B2 | 11/2003 | Schweers et al. |
| 6,781,018 B2 | 8/2004 | Liu et al. |
| 7,301,055 B2 | 11/2007 | Hoffmockel et al. |
| 7,390,932 B2 | 6/2008 | Stroefer et al. |

(Continued)

FOREIGN PATENT DOCUMENTS

| | | |
|---|---|---|
| AT | 252913 | 3/1967 |
| CN | 101665409 | 3/2010 |

(Continued)

OTHER PUBLICATIONS

Cao et al., 2012, caplus an 2012:1246481.*
Drent et al., 2001, caplus an 2001:507659.*
Chen et al., 2010, caplus an 2010:312723.*
Ionic-liquid, 2016, https://en.wikipedia.org/wiki/Ionic_liquid.*
New Jersey Department of Health and Senior Services, Hazardous Substance Fact Sheet. "Boron Trifluoride Diethyl Etherate." (c) Apr. 2000. Available from : <http://nj.gov/health/eoh/rtkweb/documents/fs/0248.pdf>.

(Continued)

*Primary Examiner* — Sun Jae Yoo

(74) *Attorney, Agent, or Firm* — Dority & Manning, P.A.

(57) ABSTRACT

The present invention relates to a process for producing cyclic acetal comprising i) preparing a liquid reaction mixture comprising a) formaldehyde source, b) an aprotic compound and c) a catalyst; and ii) converting the formaldehyde source into cyclic acetals.

23 Claims, No Drawings

(56) References Cited

U.S. PATENT DOCUMENTS

| | | |
|---|---|---|
| 7,598,402 B2 | 10/2009 | Chen et al. |
| 9,469,624 B2 * | 10/2016 | Haubs .................... C08G 65/30 |
| 2006/0058537 A1 | 3/2006 | Haubs et al. |
| 2006/0185513 A1 | 8/2006 | Stroefer et al. |
| 2008/0234459 A1 | 9/2008 | Lang et al. |
| 2010/0004409 A1 | 1/2010 | Schwittay et al. |
| 2010/0121081 A1 | 5/2010 | Lang et al. |
| 2010/0145079 A1 | 6/2010 | Stroefer et al. |
| 2014/0323686 A1 * | 10/2014 | Kurz et al. .................... 528/408 |
| 2014/0329988 A1 * | 11/2014 | Haubs et al. ................. 528/403 |
| 2014/0343300 A1 * | 11/2014 | Haubs et al. ................. 549/368 |
| 2014/0343301 A1 * | 11/2014 | Haubs et al. ................. 549/368 |
| 2014/0343302 A1 * | 11/2014 | Haubs et al. ................. 549/368 |
| 2014/0350216 A1 * | 11/2014 | Haubs et al. ................. 528/403 |

FOREIGN PATENT DOCUMENTS

| | | |
|---|---|---|
| DE | 4137846 | 5/1993 |
| DE | 19822598 | 11/1999 |
| GB | 1012372 | 12/1965 |
| GB | 1130513 | 10/1968 |
| GB | 1524440 | 9/1978 |

OTHER PUBLICATIONS

International Search Report and Written Opinion for application PCT/EP2012/073539 dated Jan. 2, 2013.
Yamaguchi T. et al: "Sythesis of cyclooligomers of formaldehyde in liquid sulfur dioxide", Chemistry and Industry, vol. 43, Oct. 23, 1971 (Oct. 23, 1971) pp. 1226-1227, XP008149518, Society of Chemical Industry, London; GB ISSN: 0009-3068.
Shoujin Su, Philippe Zaza and Albert Renken: Catalytic Dehydrogenation of Methanol to Water-Free Formaldehyde, Chem. Eng. Technol. 17 (1994) pp. 34-40.
Co pending U.S. Appl. No. 13/359,223, filed May 19, 2014.
Co pending U.S. Appl. No. 14/359,203, filed May 19, 2014.
Co pending U.S. Appl. No. 14/359,308, filed May 20, 2014.
Co pending U.S. Appl. No. 14/359,314, filed May 20, 2014.
Co pending U.S. Appl. No. 14/359,333, filed May 20, 2014.
Co pending U.S. Appl. No. 14/359,594, filed May 21, 2014.
Abstract of Japanese Patent—JPH06228126, Aug. 16, 1994, 1 page.
Abstract of Japanese Patent JP2007230979, Sep. 13, 2007, 2 pages.
JP S47-007029 B.
JP S46-031867 B.
JP S37-011033 B.

* cited by examiner

US 9,604,956 B2

PROCESS FOR THE PRODUCTION OF TRIOXANE

This present application claims priority to PCT International Patent Application No, PCT/EP2012/073539 having a filing date of Nov. 23, 2012, and which claims filing benefit to European Patent Application No. 11190586.5 filed on Nov. 24, 2011, European Patent Application No, 11190574.1 filed on Nov. 24, 2011, and European Patent Application No, 11190567.5 filed on Nov. 24, 2011, which are all hereby incorporated by reference in their entirety.

The present invention relates to a process for producing cyclic acetal comprising preparing a liquid reaction mixture comprising a formaldehyde source, an aprotic compound and a catalyst and converting the formaldehyde source in the reaction mixture to cyclic acetals. Further, the invention relates to a liquid reaction mixture.

1,3,5-Trioxane (hereinafter "trioxane") is the cyclic trimer of formaldehyde. Trioxane is mainly used as a starting material for the manufacturing of polyoxymethylenes (POM) which is a high performance polymer having desirable and exceptional properties in terms of mechanical, chemical and temperature stability. Polyoxymethylene polymers are available as homo- and copolymers.

As the polyoxymethylene market is growing there is a desire on the side of the trioxane producers to expand their production capacities in order to satisfy the trioxane demand on a competitive basis. The major technical process for the production of trioxane is the conversion of aqueous formaldehyde solutions in the presence of concentrated sulfuric acid as a catalyst. The process for the production of trioxane known in the prior art is complex and comprises an extraction step which necessitates tedious solvent recovery steps. Furthermore, the process known in the prior art is time and energy consuming and leads to a low degree of conversion of the formaldehyde source into the desired cyclic acetals (final conversion of less than 10% in the liquid reaction mixture). Furthermore, the amount of side products formed by the process is high.

Technically, the process for the production of trioxane in a liquid system is generally the conversion of an aqueous formaldehyde solution in the presence of sulfuric acid or other homogeneous or heterogeneous catalysts. However, said technical process has various draw backs.

Under the reaction conditions several side reactions do occur such as the disproportionation of the formaldehyde to formic acid and methanol (Cannizzaro reaction). The formed acid and methanol may further react to methyl formiate. Further, the work up procedure and the separation of the cyclic acetals, in particular the trioxane, is very time and energy consuming, complex and cost intensive. A typical process for the production of trioxane starts with an aqueous formaldehyde solution which is concentrated by distillation in a first step in order to remove the volume of water. Subsequently, the concentrated formaldehyde solution is fed into a reactor and converted into trioxane in the presence of a catalyst. The trioxane is separated from the reaction mixture by distillation. However, since the trioxane forms an azeotrope with the water contained in aqueous medium a subsequent extraction step and a further distillation step to remove the extracting solvent is necessary. A characteristic of this process is the high energy consumption for evaporating water which is introduced into the process by the feed stock streams.

There are various proposals for preparing trioxane from formaldehyde by gas-phase trimerization. U.S. Pat. No. 5,508,448 discloses a process for the preparation of trioxane from formaldehyde in the gas phase which process comprises contacting the formaldehyde with a solid catalyst comprising vanadyl hydrogenphosphate hemihydrates in the gas phase.

However, the gas phase processes generally lead to a low conversion of the formaldehyde source into the cyclic acetal. Furthermore, gas reactions require expensive reaction equipment such as pressure resistant vessels and, above all, the reactions are difficult to control.

Thus, the methods for the production of trioxane known in the prior art require several costly separation steps and are less efficient.

It was an object of the present invention to provide a process for the production of cyclic acetals which is more efficient, leads to a higher final conversion and produces cyclic acetals with less side products. Further, it was an object of the invention to provide a process for the production of cyclic acetals in a liquid system wherein the energy consumption is reduced and the separation of the cyclic acetals is less complex.

It has been surprisingly found that the problems associated with the methods disclosed in the prior art can be overcome by forming trioxane and other cyclic acetals derived from formaldehyde in the presence of an aprotic compound. Further, it has been found that the conversion from a formaldehyde source to cyclic acetals such as trioxane can be significantly increased.

Accordingly, in a first embodiment the present invention is directed to a process for producing cyclic acetal comprising
i) preparing a liquid reaction mixture comprising
  a) a formaldehyde source,
  b) an aprotic compound and
  c) a catalyst; and
ii) converting the formaldehyde source into cyclic acetals.

A further embodiment of the present invention is a process for producing cyclic acetal comprising reacting a formaldehyde source in the presence of a catalyst wherein the reaction is carried out in a liquid medium comprising an aprotic compound.

An alternative embodiment of the present invention is a process for producing cyclic acetal from a formaldehyde source in the presence of a catalyst and a liquid medium comprising an aprotic compound.

A further embodiment of the present invention is a liquid reaction mixture comprising
a) a formaldehyde source,
b) an aprotic compound and
c) a catalyst.

According to a preferred embodiment of the invention the liquid medium is the aprotic compound.

Thus, further embodiments of the present invention are a process for producing cyclic acetal comprising reacting a formaldehyde source in the presence of a catalyst wherein the reaction is carried out in a liquid aprotic compound or, phrased differently, a process for producing cyclic acetal from a formaldehyde source in the presence of a catalyst and a liquid aprotic compound.

A further alternative embodiment is a process for producing cyclic acetal comprising
i) preparing a liquid mixture (A) comprising
  a) a formaldehyde source and
  b) an aprotic compound; and
ii) adding a catalyst to the liquid mixture (A); and
iii) converting the formaldehyde source into cyclic acetals.

A further embodiment is a process for producing cyclic acetal comprising i) preparing a liquid mixture (A) comprising
   a) a formaldehyde source and
   b) an aprotic compound;
ii) contacting the liquid mixture (A) with a catalyst; and
iii) converting the formaldehyde source to cyclic acetal.

The term "liquid" used in the present invention in conjunction with the aprotic compound, the medium, the mixture (A) and the reaction mixture refers to the reaction conditions. Under the reaction conditions the liquid system in which the reaction of the formaldehyde source to the cyclic acetal is carried out must be liquid.

An advantage of the present invention is that the conversion of the formaldehyde source is carried out in a liquid system, e.g., a liquid reaction mixture or a liquid medium or a liquid mixture (A). However, even though it is advantageous the components of the reaction mixture or the liquid mixture (A) must not necessarily completely be dissolved. Thus the reaction mixture or the liquid mixture (A) may also comprise solids or molten components which are not dissolved.

The formaldehyde source reacts (converts) in the presence of a catalyst. Usually, cationic catalysts, such as Bronsted acids or Lewis acids, accelerate the conversion of the formaldehyde source to the desired cyclic acetals.

The catalyst is a catalyst for the conversion (reaction) of a formaldehyde source into cyclic acetals, in particular into trioxane and/or tetroxane.

The methods of the present invention refer to the production of cyclic acetals. Cyclic acetals within the meaning of the present invention relate to cyclic acetals derived from formaldehyde. Typical representatives are showing the following formula:

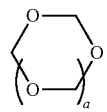

wherein a is an integer ranging from 1 to 3.

Preferably, the cyclic acetals produced by the process of the present invention are trioxane (a=1) and/or tetroxane (a=2). Trioxane and Tetroxane usually form the major part (at least 80 wt.-%, preferably at least 90 wt.-%) of the cyclic acetals formed by the process of the present invention.

The weight ratio of trioxane to tetroxane varies with the catalyst used. Typically, the weight ratio of trioxane to tetroxane ranges from about 3:1 to about 40:1, preferably about 4:1 to about 20:1.

An essential feature of the process and the reaction mixture and the liquid mixture (A) of the present invention is the aprotic compound. Contrary to protic compounds such as acids, alcohols and water having protons which can be removed relatively easy from the hetero atoms, aprotic compounds preferably have only hydrogen atoms which are linked to carbon atoms (F. A. Carey, R. J. Lundberg, Organische Chemie, Verlag VCH, 1995, page 224). Generally, aprotic compounds do not contain hydrogen atoms which can dissociate i.e., form protons under the reaction conditions.

Advantageously, the aprotic compound does not essentially deactivate the catalyst. Generally, the catalysts used for the formation of cyclic acetals from a formaldehyde source are cationic catalysts, such as Bronsted acids or Lewis acids. Preferably, under the reaction conditions the aprotic compound does essentially not deactivate the catalyst used in the process of the present invention. Aprotic solvents such as dimethylformamide (DMF), dimethylacetamide (DMAC) or N-methylpyrrolidone (NMP) are too basic and therefore may deactivate the catalyst and, as a consequence, said solvents are less suitable. According to a preferred embodiment of the present invention the liquid reaction mixture is essentially free of amides, preferably essentially free of acylic or cyclic amides. Essentially free means that the amides may be present in an amount of less than about 5 wt.-%, preferably less than about 2 wt.-%, more preferably less than 0.5 wt.-%, especially less than about 0.01 wt.-% and, in particular, less than 0.001 wt.-% or about 0 wt.-%, wherein the weight is based on the total weight of the liquid reaction mixture. Within the meaning of the present invention the aprotic compound does not deactivate the catalyst if under the reaction conditions less than about 95%, preferably less than about 50%, more preferably less than about 10%, of the Bronsted acid catalyst used protonates the aprotic compound. In case a Lewis acid catalyst is used the aprotic compound does not deactivate the catalyst if under the reaction conditions less than about 90 wt-%, preferably less than about 50 wt.-%, more preferably less than about 10 wt-% of the Lewis acid catalyst forms a complex with the aprotic compound.

The degree of protonation and complex formation can be determined by NMR spectroscopy such as $^1$H or $^{13}$C-NMR. The degree of protonation and complex formation is determined at 25° C., preferably in $d_6$-DMSO.

The deactivation of the catalyst can also be determined in the following manner:

10 g of commercially available paraformaldehyde (95 wt %) is dissolved in 100 g of sulfolane at a temperature sufficient to dissolve the paraformaldehyde in such a way that no gaseous formaldehyde can escape. The clear solution is kept at 90° C. and 0.1 wt % of triflic acid is added. The rate of the formation of trioxane is measured (by measuring the concentration of trioxane as a function of time).

The same experiment is repeated, except that 10 g of the sulfolane are replaced by 10 g of the aprotic compound to be tested. If the rate of trioxane formation is still greater than about 1%, preferably greater than about 5%, more preferably greater than about 10%, of the rate of the initial experiment then it is concluded that the aprotic compound in question does not deactivate the catalyst (even though it may reduce its activity).

The aprotic compound should not be too basic in order to avoid deactivation of the catalysts. On the other hand the aprotic compound preferably does not chemically react with the formaldehyde source under the reaction conditions.

Preferably, under the reaction conditions the aprotic compound should not react chemically with the formaldehyde source or the cyclic acetal obtained by the process of the invention. Compounds like water and alcohols are not suitable as they react with formaldehyde. Within the meaning of the present invention an aprotic compound does not chemically react with the formaldehyde source when it meets the following test criteria:

5 g of commercially available paraformaldehyde (95 wt.-%) is added to 100 g of the aprotic compound containing 0.1 wt.-% trifluoromethanesulfonic acid and heated at 120° C. for 1 hour with stirring in a closed vessel so that no gaseous formaldehyde can escape. If less than about 1 wt.-%, preferably less than about 0.5 wt.-%, more preferably less than about 0.1 wt.-% and most preferably less than about 0.01 wt.-% of the aprotic compound has chemically reacted, then the aprotic compound is considered not to have reacted with the formaldehyde source.

Further, under the acidic reaction conditions the aprotic compound should be essentially stable. Therefore, aliphatic ethers or acetals are less suitable as aprotic compounds. The aprotic compound is considered stable under acidic conditions within the meaning of the present invention if the aprotic compound meets the following test conditions:

100 g of the aprotic compound to be tested containing 0.5% by weight (wt.-%) trifluoromethanesulfonic acid is heated at 120° C. for 1 hour. If less than about 0.5 wt.-%, preferably less than about 0.05 wt.-%, more preferably less than about 0.01 wt.-% and most preferably less than about 0.001 wt.-% of the aprotic compound has chemically reacted, then the aprotic compound is considered to be stable under acidic conditions.

According to a preferred embodiment of the present invention the aprotic compound is liquid under the reaction conditions. Therefore, the aprotic compound may have a melting point of about 180° C. or less, preferably about 150° C. or less, more preferably about 120° C. or less, especially about 60° C. or less.

For practical reasons it is advantageous to use an aprotic compound which has a melting point in the order of preference (the lower the melting point the more preferred) of below about 50° C., below about 40° C. and below about 30° C. and below about 20° C. Especially, aprotic compounds which are liquid at about 25 or about 30° C. are suitable since they can easily transported by pumps within the production plant.

Further, the aprotic compound may have a boiling point of about 120° C. or higher, preferably about 140° C. or higher, more preferably about 160° C. or higher, especially about 180° C. or higher, determined at 1 bar. The higher the boiling point the better the cyclic acetals, especially trioxane and/or tetroxane formed by the process of the present invention can be separated by distillation. Therefore, according to an especially preferred embodiment of the present invention the boiling point of the aprotic compound is at least about 20° C. higher than the boiling point of the cyclic acetal formed, in particular at least about 20° C. higher than the boiling point of trioxane and/or tetroxane.

Additionally, aprotic compounds are preferred which do not form an azeotrope with the cyclic acetal, especially do not form an azeotrope with trioxane.

In a preferred embodiment of the present invention the reaction mixture comprises at least about 20 wt.-%, preferably at least about 40 wt.-%, more preferably at least about 60 wt.-%, most preferably at least about 80 wt.-% and especially at least about 90 wt.-% of the aprotic compound(s), wherein the weight is based on the total weight of the reaction mixture. The liquid medium or the reaction mixture or the liquid mixture (A) may comprise one or more aprotic compound(s).

In a preferred embodiment the liquid medium is essentially consisting of the aprotic compound. Essentially consisting of means that the liquid medium comprises at least about 95 wt.-%, preferably at least about 98 wt.-%, more preferably at least about 99 wt.-%, especially at least about 99.5 wt.-%, in particular at least about 99.9 wt.-% of the aprotic compound(s). In a further embodiment of the invention the liquid medium is the aprotic compound, i.e., the liquid medium is consisting of the aprotic compound.

It has been found that liquid aprotic compounds which at least partly dissolve the formaldehyde source lead to excellent results in terms of conversion of the formaldehyde source into the desired cyclic acetals.

Therefore, aprotic compounds are preferred which at least partly dissolve the formaldehyde source under the reaction conditions. Preferred are aprotic compounds which dissolve paraformaldehyde (98 wt.-% formaldehyde, 2 wt.-% water) [can also be expressed as Pn=moles of formaldehyde/moles of water=(98/30)/(2/8)=approx. 29] at the reaction temperature in an amount of at least about 0.1 wt.-%, wherein the weight is based on the total weight of the solution.

Further, preferably the aprotic compound dissolves paraformaldehyde (98 wt.-% formaldehyde, 2 wt.-% water; Pn=approx. 29) at 120° C. in an amount of at least about 1 wt.-%, preferably at least about 5 wt.-% and more preferably at least about 10 wt.-%, wherein the weight is based on the total weight of the solution.

The aprotic compound used in the process of the invention or the reaction mixture or the liquid mixture (A) of the present invention is preferably a polar aprotic compound. Polar aprotic solvents are much more suitable to dissolve the formaldehyde source. Unpolar aprotic compounds such as unsubstituted hydrocarbons (e.g. cyclic hydrocarbons such as cyclohexane, or alicyclic hydrocarbons such as hexane, octane, decane, etc.) or unsubstituted unsaturated hydrocarbons or unsubstituted aromatic compounds are less suitable. Therefore, according to a preferred embodiment the aprotic compound is not an unsubstituted hydrocarbon or unsubstituted unsaturated hydrocarbon or unsubstituted aromatic compound. Further, preferably the reaction mixture comprises unsubstituted hydrocarbons and/or unsubstituted unsaturated hydrocarbons and/or unsubstituted aromatic compounds in an amount of less than about 50 wt.-%, more preferably less than about 25 wt.-%, further preferably less than about 10 wt.-%, especially less than about 5 wt.-%, e.g. less than about 1 wt.-% or about 0 wt.-%.

Polar aprotic compounds are especially preferred. According to a preferred embodiment of the invention the aprotic compound has a relative static permittivity of more than about 15, preferably more than about 20, more preferably of more than about 25, especially of more than about 30, determined at 25° C.

The relative static permittivity, $\varepsilon_r$, can be measured for static electric fields as follows: first the capacitance of a test capacitor $C_0$, is measured with vacuum between its plates. Then, using the same capacitor and distance between its plates the capacitance $C_x$ with an aprotic compound between the plates is measured. The relative dielectric constant can be then calculated as $$\varepsilon_r = \frac{C_x}{C_0}.$$

Preferred are aprotic compounds which dissolve the formaldehyde source.

According to a preferred embodiment the formaldehyde source is at least partially, preferably at least about 80 wt.-%, more preferably at least about 95 wt.-%, especially completely, in solution in the reaction mixture or liquid mixture (A).

Therefore the process of the invention is preferably carried out in manner wherein the formaldehyde source is completely dissolved in the liquid medium or reaction mixture or liquid mixture (A).

Therefore, according to a preferred embodiment the formaldehyde source and the aprotic compound form a homogenous phase under the reaction conditions.

Suitable aprotic compounds are selected from the group consisting of organic sulfoxides, organic sulfones, organic sulfonate ester, nitrile group containing organic compounds, halogenated aromatic compounds, nitro group containing aromatic compounds and mixtures thereof.

According to a preferred embodiment the aprotic compound is selected from sulfur containing organic compounds.

Further, the aprotic compound is preferably selected from the group consisting of cyclic or alicyclic organic sulfoxides, alicyclic or cyclic sulfones, organic mono- or di-nitrile compounds, nitrobenzene and mixtures thereof.

Excellent results can be achieved by aprotic compounds as represented by the following formula (I):

(I)

wherein
n is an integer ranging from 1 to 6, preferably 2 or 3, and
wherein the ring carbon atoms may optionally be substituted by one or more substituents, preferably selected from $C_1$-$C_8$-alkyl which may be branched or unbranched.

According to the most preferred embodiment the aprotic compound is sulfolane (tetrahydrothiophene-1,1-dioxide).

Sulfolane is an excellent solvent for the formaldehyde source, it is stable under acidic conditions, it does not deactivate the catalysts and it does not form an azeotrope with trioxane.

Unless indicated otherwise the expression "reaction mixture" refers to the mixture which is used for the reaction of the formaldehyde source to the cyclic acetals. The concentrations and amounts of the individual components of the reaction mixture refer to the concentrations and amounts at the beginning of the reaction. In other words the reaction mixture is defined by the amounts of its starting materials, i.e. the amounts of initial components.

Likewise the amounts defined for the "liquid mixture (A)" refer to the amounts of the components at the beginning of the reaction, i.e. prior to the reaction.

The formaldehyde source reacts to the cyclic acetals and, as a consequence, the concentration of the formaldehyde source decreases while the concentration of the cyclic acetals increases.

At the beginning of the reaction a typical reaction mixture of the invention comprises
a formaldehyde source,
a) a catalyst and
b) sulfolane.

Further, an especially preferred embodiment of the present invention is a process for producing cyclic acetal comprising reacting a formaldehyde source in the presence of a catalyst wherein the reaction is carried out in sulfolane or a process for producing cyclic acetal from a formaldehyde source in the presence of a catalyst and sulfolane.

A further preferred aprotic compound is represented by formula (II):

(II)

wherein $R^1$ and $R^2$ are independently selected from $C_1$-$C_8$-alkyl which may be branched or unbranched, preferably wherein $R^1$ and $R^2$ independently represent methyl or ethyl. Especially preferred is dimethyl sulfone.

According to a further preferred embodiment the aprotic compound is represented by formula (III):

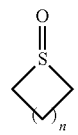

(III)

wherein
n is an integer ranging from 1 to 6, preferably 2 or 3, and
wherein the ring carbon atoms may optionally be substituted by one or more substituents, preferably selected from $C_1$-$C_8$-alkyl which may be branched or unbranched.

Suitable aprotic compounds are also represented by formula (IV):

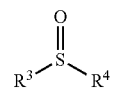

(IV)

wherein $R^3$ and $R^4$ are independently selected from $C_1$-$C_8$-alkyl which may be branched or unbranched, preferably wherein $R^1$ and $R^2$ independently represent methyl or ethyl.

Especially preferred is dimethyl sulfoxide.

Suitable aprotic compounds may be selected from aliphatic dinitriles, preferably adiponitrile.

The reaction mixture typically comprises the aprotic compound in an amount ranging from about 20 to about 99.85 wt.-%, preferably from about 30 to about 99.5 wt.-% or about 30 to about 98 wt.-%, more preferably from about 40 to about 99 wt.-%, further preferably from about 60 to about 98 wt.-%, especially from about 80 to about 97 wt.-%, based on the total weight of the reaction mixture Further, the reaction mixture specifically comprises the aprotic compound in an amount ranging from 25 to 90 wt.-%, further ranging from 25 to 75 wt.-% and in particular from 30 to 65 wt.-%, based on the total weight of the reaction mixture.

The process of the invention is carried out in the presence of a catalyst for the conversion of the formaldehyde source into cyclic acetals. Suitable catalysts are any components which accelerate the conversion of the formaldehyde source to the cyclic acetals.

The catalyst is a catalyst for the conversion (reaction) of a formaldehyde source into cyclic acetals, preferably into trioxane and/or tetroxane.

Usually, cationic catalysts can be used for the process of the invention. The formation of cyclic acetals can be heterogeneously or homogenously catalysed. In case the catalysis is heterogeneous the liquid mixture comprising the formaldehyde source and the aprotic compound is contacted with the solid catalyst or an immiscible liquid catalyst. A typical liquid immiscible catalyst is a liquid acidic ion exchange resin. Solid catalyst means that the catalyst is at least partly, preferably completely in solid form under the reaction conditions. Typical solid catalysts which may be used for the process of the present invention are acid ion-exchange material, Lewis acids and/or Bronsted acids fixed on a solid support, wherein the support may be an inorganic material such as $SiO_2$ or organic material such as organic polymers.

However, preferred is a homogenous catalysis wherein the catalyst is dissolved in the reaction mixture.

Preferred catalysts are selected from the group consisting of Bronsted acids and Lewis acids. The catalyst is preferably selected from the group consisting of trifluoromethanesulfonic acid, perchloric acid, methanesulfonic acid, toluenesulfonic acid and sulfuric acid, or derivatives thereof such as anhydrides or esters or any other derivatives that generate the corresponding acid under the reaction conditions. Lewis acids like boron trifluoride, arsenic pentafluoride can also be used. It is also possible to use mixtures of all the individual catalysts mentioned above.

The catalyst is typically used in an amount ranging from about 0.001 to about 15 wt %, preferably about 0.01 to about 5 wt % or about 0.01 to about 10 wt.-%, more preferably from about 0.05 to about 2 wt % and most preferably from about 0.05 to about 0.5 wt %, based on the total weight of the reaction mixture.

The formaldehyde source used in the process and reaction mixture and liquid mixture (A) of the present invention can in principle be any compound which can generate formaldehyde or which is formaldehyde or an oligomer or (co)-polymer thereof.

According to a preferred embodiment the formaldehyde source is gaseous formaldehyde.

Gaseous formaldehyde typically comprises traces of water. According to a preferred embodiment the water content is less than about 5 wt.-%, preferably less than about 2 wt.-%, more preferably less than about 1 wt.-%, especially less than about 0.5 wt.-%, wherein the weight is based on the total weight of the sum of the formaldehyde source and the water.

A further preferred formaldehyde source is paraformaldehyde.

Preferably, the paraformaldehyde used has a water content of less than about 5 wt.-%, preferably less than about 2 wt.-%, more preferably less than about 1 wt.-%, especially less than about 0.5 wt.-%, wherein the weight is based on the total weight of the sum of the formaldehyde source and water.

Another preferred formaldehyde source comprises polyoxymethylene homo- and/or copolymers, preferably with a number average molecular weight (Mn) of more than 2000 Dalton.

The molar mass is determined by GPC (gel permeation chromatography):
Eluent: hexafluoroisopropanol+0.05% of trifluoroacetic acid potassium salt
Column temperature: 40° C.
Flow rate: 0.5 ml/min
Detector: differential refractometer Agilent G1362A.

The calibration was effected using PMMA standards having a narrow distribution from PSS, with molecular weights of M=505 to M=2 740000. Elution ranges outside this interval were estimated by extrapolation.

A further preferred formaldehyde source is formaldehyde which may be present in an aqueous solution. The formaldehyde content of the aqueous formaldehyde solution is preferably ranging from about 60 to about 90 wt.-%, more preferably ranging from about 65 to about 85 wt.-%, based on the total weight of the aqueous formaldehyde solution.

The process of the invention can also be used to change the ratio of cyclic acetals derived from formaldehyde. Therefore, the formaldehyde source can also comprise cyclic acetals selected from the group consisting of trioxane, tetroxane and cyclic oligomers derived from formaldehyde.

Of course, any mixtures of the above-mentioned formaldehyde sources can also be used.

Preferably, the reaction mixture comprises the formaldehyde source in an amount ranging from about 0.1 to about 80 wt % or about 1 to less than about 80 wt.-%, more preferably from about 5 to about 75 wt %, further preferably ranging from about 10 to about 70 wt % and most preferred ranging from about 20 to about 70 wt %, especially ranging from 30 to 60 wt.-% based on the total weight of the reaction mixture.

According to a preferred embodiment the weight ratio of formaldehyde source to aprotic compound is ranging from about 1:1000 to about 4:1, preferably about 1:600 to about 3:1, more preferably about 1:400 to about 2:1, further preferably about 1:200 to about 1:1, especially preferably about 1:100 to about 1:2, particularly about 1:50 to about 1:3, for example about 1:20 to about 1:6 or about 1:15 to about 1:8.

It has been found that protic compounds in the reaction mixture decrease the degree of conversion. Therefore, it is desired that the amount of protic compounds is as low as possible.

According to a preferred embodiment of the present invention the amount of protic compounds, in particular the amount of water and alcohols, is less than about 20 wt.-%, preferably less than about 15 wt.-%, more preferably less than about 10 wt.-%, further preferably less than about 5 wt.-%, especially preferably less than about 2 wt.-%, in particular less than about 1 wt.-%, for example less than about 0.5 wt.-%, based on the total amount of the liquid reaction mixture.

According to an especially preferred embodiment of the invention the amount of water in the reaction mixture is less than about 20 wt.-%, preferably less than about 15 wt.-%, more preferably less than about 10 wt.-%, further preferably less than about 5 wt.-%, especially preferably less than about 2 wt.-%, in particular less than about 1 wt.-%, for example less than about 0.5 wt.-%, based on the total amount of the liquid reaction mixture.

A preferred embodiment of the process of the present invention is a process for producing cyclic acetal comprising
i) preparing a liquid reaction mixture comprising
  a) 0.1 to less than 80 wt.-% of a formaldehyde source,
  b) 20 to 99.85 wt.-% of an aprotic compound and
  c) 0.001 to 15 wt % of a catalyst; and
ii) converting the formaldehyde source into cyclic acetals.

An especially preferred embodiment of the present invention is a process for producing cyclic acetal, preferably trioxane and/or tetroxane, comprising
i) preparing a liquid reaction mixture comprising
  a) 20 to 70 wt.-%, preferably 30 to 60 wt.-%, of a formaldehyde source, preferably selected from the group consisting of gaseous formaldehyde, paraformaldehyde, polyoxymethylene homo- and copolymers, an aqueous formaldehyde solution, trioxane, tetroxane, cyclic oligomers derived from formaldehyde and mixtures thereof b) 25 to 75 wt.-%, preferably 30 of 65 wt.-%, of an aprotic compound, preferably selected from sulfolane, dimethyl sulfoxide, dimethyl sulfone and nitrobenzene, especially sulfolane;

c) 0.001 to 10 wt % of a catalyst, preferably selected from Bronsted and Lewis acids; and d) optional less than 20 wt.-% of water; and ii) converting the formaldehyde source into cyclic acetals, preferably trioxane and/or tetroxane.

Typically, the reaction is carried out at a temperature higher than about 0° C., preferably ranging from about 0° C. to about 150° C., more preferably ranging from about 10° C. to about 120° C., further preferably from about 20° C. to about 100° C. and most preferably from about 30° C. to about 90° C.

A further advantageous of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals are used the formed cyclic acetals can simply be distilled off. In case sulfolane is used as the aprotic compound the formed trioxane can be distilled off without the formation of an azeotrope of sulfolane with trioxane. The process of the invention can be carried out batch wise or as a continuous process.

In a preferred embodiment the process is carried out as a continuous process wherein the formaldehyde source is continuously fed to the liquid medium comprising the catalyst and wherein the cyclic acetals, e.g. the trioxane, is continuously separated by separation methods such as distillation.

The process of the invention leads to an extremely high conversion of the formaldehyde source to the desired cyclic acetals. Conversions higher than 10 for the production of trioxane in liquid media are not known in the prior art.

According to a preferred embodiment the final conversion of the formaldehyde source to the cyclic acetal is greater than 10%, based on initial formaldehyde source.

The final conversion refers to the conversion of the formaldehyde source into the cyclic acetals in the liquid system. The final conversion corresponds to the maximum conversion achieved in the liquid system.

The final conversion of the formaldehyde source to the cyclic acetals can be calculated by dividing the amount of cyclic acetals (expressed in wt.-%, based on the total weight of the reaction mixture) in the reaction mixture at the end of the reaction divided by the amount of formaldehyde source (expressed in wt.-%, based on the total weight of the reaction mixture) at the beginning of the reaction at t=0.

For example the final conversion of the formaldehyde source to trioxane can be calculated as:

Final conversion=(amount of trioxane in the reaction mixture expressed in weight-% at the end of the reaction) (amount of formaldehyde source in the reaction mixture expressed in weight-% at $t=0$ [initial amount of formaldehyde source in the reaction mixture])

According to a further preferred embodiment of the process of the invention the conversion which can e.g. be the final conversion of the formaldehyde source into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

Preferably, at least partially converting the formaldehyde source into the cyclic acetal means that the conversion of the formaldehyde source into the cyclic acetals, preferably trioxane and/or tetroxane, is greater than 10%, based on the initial formaldehyde source, especially higher than 12%, preferably higher than 14%, more preferably higher than 16%, further preferably higher than 20%, especially higher than 30%, particularly higher than 50%, for example higher than 80% or higher than 90%.

The liquid reaction mixture of the present invention comprises a) a formaldehyde source, b) an aprotic compound and c) a catalyst.

The preferred amounts and components a) to c) are described throughout the description of the present invention.

Especially preferred is a liquid reaction mixture comprising a) 5 to 70 wt.-%, preferably 20 to 70 wt.-%, more preferably 30 to 60 wt.-%, of a formaldehyde source, preferably selected from the group consisting of gaseous formaldehyde, paraformaldehyde, polyoxymethylene homo- and copolymers, an aqueous formaldehyde solution, trioxane, tetroxane, cyclic oligomers derived from formaldehyde and mixtures thereof, b) 25 to 90 wt.-%, preferably 25 to 75 wt.-%, more preferably 30 of 65 wt.-%, of an aprotic compound, preferably selected from sulfolane, dimethyl sulfoxide, dimethyl sulfone and nitrobenzene, especially sulfolane;

c) 0.001 to 10 wt % of a catalyst, preferably selected from Bronsted and Lewis acids; and d) optional less than 20 wt.-% of water, wherein the amounts are based on the total weight of the reaction mixture.

A further embodiment of the present invention is a liquid mixture (A) comprising a) a formaldehyde source and b) an aprotic compound.

The preferred components a) and b) for the liquid mixture (A) of the invention are described throughout the description of the present invention.

Preferably, the liquid mixture (A) comprises the formaldehyde source in an amount ranging from about 0.1 to about 80 wt.-% or about 1 to less than about 80 wt.-%, more preferably from about 5 to about 75 wt.-%, further preferably ranging from about 10 to about 70 wt % and most preferred ranging from about 20 to about 70 wt.-%, especially ranging from 30 to 60 wt.-% based on the total weight of the liquid mixture (A).

The liquid mixture (A) typically comprises the aprotic compound in an amount ranging from about 20 to about 99.85 wt.-%, preferably from about 30 to about 99.5 wt.-% or about 30 to about 98 wt.-%, more preferably from about 40 to about 99 wt.-%, further preferably from about 60 to about 98 wt.-%, especially from about 80 to about 97 wt.-%, based on the total weight of the liquid mixture (A).

Further the reaction mixture specifically comprises the aprotic compound in an amount ranging from about 25 to about 90 wt.-%, further ranging from about 25 to about 75 wt.-% and in particular from about 30 to about 65 wt.-%, based on the total weight of the liquid mixture (A).

According to a preferred embodiment of the present invention the amount of protic compounds, in particular the amount of water and alcohols, in the liquid mixture (A) is less than about 20 wt.-%, preferably less than about 15 wt.-%, more preferably less than about 10 wt.-%, further preferably less than about 5 wt.-%, especially preferably less than about 2 wt.-%, in particular less than about 1 wt.-%, for example less than about 0.5 wt.-%, based on the total amount of the liquid mixture (A).

According to an especially preferred embodiment of the invention the amount of water in the liquid mixture (A) is less than about 20 wt.-%, preferably less than about 15 wt.-%, more preferably less than about 10 wt.-%, further preferably less than about 5 wt.-%, especially preferably less than about 2 wt.-%, in particular less than about 1 wt.-%, for example less than about 0.5 wt.-%, based on the total amount of the liquid mixture (A).

A further embodiment is a process for producing cyclic acetal comprising i) preparing a liquid mixture (A) comprising
   a) a formaldehyde source and
   b) an aprotic compound;
ii) contacting the liquid mixture (A) with a catalyst; and
iii) converting the formaldehyde source into cyclic acetal.

According to this embodiment of the present invention a liquid mixture (A) as defined above can be prepared and contacted with a catalyst as defined above. According to a preferred embodiment the catalyst is a solid catalyst which at least remain partly solid under the reaction conditions. Preferably the catalyst is selected from fixed bed catalyst, acid ion-exchange material and solid support carrying Bronsted and/or Lewis acids.

The liquid mixture (A) is preferably comprising a) 5 to 70 wt.-%, preferably 20 to 70 wt.-%, more preferably 30 to 60 wt.-%, of a formaldehyde source, preferably selected from the group consisting of gaseous formaldehyde, paraformaldehyde, polyoxymethylene homo- and copolymers, an aqueous formaldehyde solution, trioxane, tetroxane, cyclic oligomers derived from formaldehyde and mixtures thereof, b) 25 to 90 wt.-%, preferably 25 to 75 wt.-%, more preferably 30 of 65 wt.-%, of an aprotic compound, preferably selected from sulfolane, dimethyl sulfoxide, dimethyl sulfone and especially sulfolane;

c) optional 0.001 to 10 wt % of a catalyst, preferably selected from Bronsted and Lewis acids; and d) optionally less than 20 wt.-% of protic compounds, especially water, wherein the amounts are based on the total weight of the liquid mixture (A).

A further embodiment of the present invention is the use of an aprotic compound for the production of cyclic acetals.

The preferred aprotic compounds do not deactivate the catalyst, do not form an azeotrope with trioxane and do have a boiling point of at least 20° C. higher than the boiling point of trioxane at 1 bar.

The preferred aprotic compounds are defined throughout the description. Preferably a polar aprotic compound, more preferably selected from the group consisting of sulfolane, dimethyl sulfoxide, dimethyl sulfone, and especially sulfolane, is used for the production of cyclic acetals, preferably trioxane and/or tetroxane.

Preferred embodiments of the present invention refer to:

1. A process for producing cyclic acetal comprising
   i) preparing a liquid reaction mixture comprising
      a) a formaldehyde source,
      b) an aprotic compound and
      c) a catalyst; and
   ii) converting the formaldehyde source into cyclic acetals.

2. A process according to item 1. wherein the aprotic compound is liquid under the reaction conditions.

3. A process according to items 1. or 2. wherein the aprotic compound has a boiling point of 120° C. or higher, preferably 140° C. or higher, more preferably 160° C. or higher, especially 180° C. or higher, determined at 1 bar.

4. A process according to one or more of the preceding items wherein the reaction mixture comprises at least 20 wt.-%, preferably at least 40 wt.-%, more preferably at least 60 wt.-%, most preferably at least 80 wt.-% and especially at least 90 wt.-% of the aprotic compound, wherein the weight is based on the total weight of the reaction mixture.

5. A process according to one or more of the preceding items wherein the aprotic compound is selected from the group consisting of organic sulfoxides, organic sulfones, organic sulfonate ester, nitrile group containing organic compounds, halogenated aromatic compounds, nitro group containing aromatic compounds and mixtures thereof, preferably the aprotic compound is selected from sulfur containing organic compounds.

6. A process according to one or more of the preceding items wherein the aprotic compound is selected from the group consisting of cyclic or alicyclic organic sulfoxides, alicyclic or cyclic sulfones, organic mono- or di-nitrile compounds, nitrobenzene and mixtures thereof.

7. A process according to one or more of the preceding items wherein the aprotic compound is represented by formula (I):

wherein
n is an integer ranging from 1 to 6, preferably 2 or 3, and
wherein the ring carbon atoms may optionally be substituted by one or more substituents, preferably selected from C1-C8-alkyl which may be branched or unbranched.

8. Process according to one or more of the preceding items wherein the aprotic compound is sulfolane.

9. Process according to one or more of items 1. to 6. wherein the aprotic compound is represented by formula (II):

wherein $R^1$ and $R^2$ are independently selected from C1-C8-alkyl which may be branched or unbranched, preferably wherein $R^1$ and $R^2$ independently represent methyl or ethyl, preferably the aprotic compound is dimethyl sulfone.

10. Process according to one or more of items 1. to 6. wherein the aprotic compound is represented by formula (III):

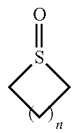

wherein
n is an integer ranging from 1 to 6, preferably 2 or 3, and wherein the ring carbon atoms may optionally be substituted by one or more substituents, preferably selected from C1-C8-alkyl which may be branched or unbranched; or the aprotic compound is represented by formula (IV):

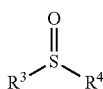

wherein $R^3$ and $R^4$ are independently selected from C1-C8-alkyl which may be branched or unbranched, preferably wherein $R^1$ and $R^2$ independently represent methyl or ethyl; preferably the aprotic compound is dimethyl sulfoxide.

11. A process according to one or more of the preceding items wherein the catalyst is selected from the group consisting of Bronsted acids and Lewis acids.

12. Process according to one or more of the preceding items wherein the formaldehyde source is selected from the group consisting of gaseous formaldehyde, paraformaldehyde, polyoxymethylene homo- and copolymers, and an aqueous formaldehyde solution and mixtures thereof.

13. Process according to one or more of the preceding items wherein the formaldehyde source and the aprotic compound form a homogenous phase.

14. Process according to one or more of the preceding items wherein the reaction is carried out at a temperature higher than 0° C., preferably ranging from 0° C. to 150° C., more preferably ranging from 10° C. to 120° C., further preferably from 20° C. to 100° C. and most preferably from 30° C. to 90° C.

15. Liquid reaction mixture comprising a formaldehyde source, a catalyst and an aprotic compound.

EXAMPLES

Example 1

Anhydrous formaldehyde was prepared by the thermal decomposition of paraformaldehyde (essay: 96 wt %, from Acros Organics) at a rate of ca. 1 g/min at appr. 120° C. and a pressure of 80 mbar. The formaldehyde gas was absorbed in a absorption column containing 500 g sulfolane (<0.1 wt % water) with 0.1 wt % triflic acid at around 40° C. After 1 hr, the sulfolane in the adsorption column was neutralized with triethylamine and analyzed by GC and sulfite titration. The following composition was found:
Trioxane: 8.3 wt %
Tetroxane: 1.1 wt %
Formaldehyde: 0.6 wt %
Methyl formate: 0.5 wt %

Final conversion of formaldehyde to trioxane in the reaction mixture: 77.5%
Final conversion of formaldehyde to trioxane and tetroxane in the reaction mixture: 88%

Example 2

500 g of an aqueous 80 wt. % solution of formaldehyde were mixed with 500 g of sulfolane at 80° C. 40 g of concentrated sulfuric acid were added and the clear mixture was heated to 100° C. and kept there for 15 min. Then 50 ml were distilled off at atmospheric pressure and analyzed:
The distillate contained:
32 wt % trioxane
0.05 wt % methyl formate Comparative Example 3

To 100 g of a 60 wt.-% solution of formaldehyde in water at 100° C. 5 g of sulfuric acid is added. After 15 min ca. 5 g were distillated off at atmospheric pressure. The trioxane concentration in the distillate was 22 wt.-%. This shows that the process of the invention is more effective and requires less energy to separate the cyclic acetal due to the higher trioxane concentration in the distillate.

Example 4

9 g of commercial paraformaldehyde with a water content of ca. 4 wt % (essay: 96 wt % from Acros Organics) were added to 91 g of sulfolane at 145° C. with stirring. As the paraformaldehyde dissolves, the temperature decreases to 122° C. The clear solution was allowed to cool to 100° C. At that temperature 0.3 ml of a 10 wt % solution of triflic acid in sulfolane was added. After 1 min, the homogeneous solution was allowed to cool to 60° C., was neutralized with triethylamine and then analyzed. The following composition was found:
Trioxane: 7.0 wt %
Tetroxane: 0.6 wt %
Formaldehyde: 1 wt %

Example 5

10 g of dried Polyoxymethylene Copolymer (with a low Dioxolane content) (TICONA trade name: Hostaform® HS 15) with melt index of 1.5 g/10 min were dissolved in 90 g of sulfolane at 145° C. with stirring. The clear solution was added to 20 g sulfolane (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 7.1 wt %
Tetroxane: 0.75 wt %
Formaldehyde: 0.4 wt %
Methylformate: <20 ppm Example 6

Example 5 was repeated, except that perchloric acid (70 wt % in water) was used for triflic acid:
10 g of dried Polyoxymethylene Copolymer (with a low Dioxolane content) (TICONA trade name: Hostaform® HS 15) with melt index of 1.5 g/10 min were dissolved in 90 g of sulfolane at 145° C. with stirring. The clear solution was added to 20 g sulfolane (at 120° C.) containing 1.2 ml of a 2 wt % solution of perchloric acid (70 wt % in water) in sulfolane. After the addition was completed, the homogeneous solution was cooled to 60° C., neutralized with triethylamine and then analyzed. The following composition was found:
Trioxane: 7.2 wt %
Tetroxane: 0.8 wt %
Formaldehyde: 0.3 wt %
Methylformate: <20 ppm Comparative Example 7

Example 5 was repeated, except that nitrobenzene was used for sulfolane as a solvent:
10 g of dried Polyoxymethylene Copolymer (with a low Dioxolane content) (TICONA trade name: Hostaform® HS 15) with melt index of 1.5 g/10 min were dissolved in 90 g of nitrobenzene at 145° C. with stirring. The clear solution was added to 20 g nitrobenzene (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 6.2 wt %
Tetroxane: 0.7 wt %
Formaldehyde: 0.7 wt %
Methylformate: 0.5 wt %
The GC spectrum also showed a new peak with a retention time beyond that of nitrobenzene, which was not further analyzed but is believed to be a reaction product of nitrobenzene with formaldehyde. Thus, nitrobenzene is not stable under reaction conditions, produces side products (methylformate) and consequently has a lower yield in trioxane.

Example 8

Example 5 was repeated, except that a mixture of Dimethylsulfone (30 g) and Sulfolane (60 g) was used for sulfolane as a solvent:
10 g of dried Polyoxymethylene Copolymer (with a low Dioxolane content) (TICONA trade name: Hostaform® HS 15) with melt index of 1.5 g/10 min were dissolved in a mixture of Dimethylsulfone (30 g) and Sulfolane (60 g) at 145° C. with stirring. The clear solution was added to 20 g sulfolane (at 120° C.) containing 0.4 ml of a 10 wt % solution of triflic acid in sulfolane. After the addition was completed, the homogeneous solution was cooled to 60° C., neutralized with triethylamine and then analyzed. The following composition was found:
Trioxane: 7.1 wt %
Tetroxane: 0.6 wt %
Formaldehyde: 0.8 wt %
Methylformate: 9.4 ppm Example 9

Example 4 was repeated except that strongly acidic ion exchange resin (Amberlyst 15®, wet form, from DOW CHEMICAL) was used instead of triflic acid as catalyst.
Before use the resin was conditioned to sulfolane (exchange of water in the pores of the resin by sulfolane)

9 g of commercial paraformaldehyde with a water content of ca. 4 wt % (essay: 96 wt % from Acros Organics) were added to 91 g of sulfolane at 145° C. with stirring. As the paraformaldehyde dissolves the temperature decreases to 122° C. The clear solution was allowed to cool to 100° C. At that temperature 10 g of Amberlyst 15® was added. After 10 min at 100° C. the reaction mixture was allowed to cool to 50° C., and no precipitate formed, indicating the conversion of the paraformaldehyde to trioxane. The concentration of the trioxane in the reaction mixture is estimated to be above 6 wt %.

The invention claimed is:
1. A process for producing a cyclic acetal comprising:
contacting a formaldehyde source with a liquid medium comprising a sulfur-containing organic compound and a catalyst, the catalyst comprising trifluoromethanesulfonic acid, perchloric acid, methanesulfonic acid, toluenesulfonic acid, sulfuric acid, or a solid acid ion-exchange materiel; and
at least partially converting the formaldehyde source into a cyclic acetal, wherein the cyclic acetal comprises trioxane.
2. A process according to claim 1, wherein the sulfur-containing organic compound has a boiling point of 140° C. or higher, determined at 1 bar.
3. A process according to claim 1 wherein higher than 10% of the formaldehyde source is converted into one or more cyclic acetals during the reaction.
4. A process according to claim 1 wherein the liquid medium comprises at least 20 wt.-%, of the sulfur-containing organic compound.
5. A process according to claim 1, wherein the sulfur-containing organic compound is selected from the group consisting of organic sulfoxides, organic sulfones, organic sulfonate esters, and mixtures thereof.
6. A process according to claim 1 wherein the sulfur-containing organic compound is selected from the group consisting of cyclic or alicyclic organic sulfoxides, alicyclic or cyclic sulfones, and mixtures thereof.
7. A process according to claim 1 wherein the sulfur-containing organic compound is represented by formula (I):

wherein
n is an integer ranging from 1 to 6, and
wherein the ring carbon atoms may optionally be substituted by one or more substituents, selected from $C_1$-$C_8$-alkyl which may be branched or unbranched or by the formula (II):

wherein $R^1$ and $R^2$ are independently selected from $C_1$-$C_8$-alkyl which may be branched or unbranched or by the formula (III):

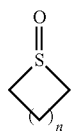

(III)

wherein n is an integer ranging from 1 to 6, and wherein the ring carbon atoms may optionally be substituted by one or more substituents, selected from $C_1$-$C_8$-alkyl which may be branched or unbranched; or by the formula (IV):

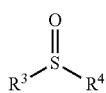

(IV)

wherein $R^3$ and $R^4$ are independently selected from $C_1$-$C_8$-alkyl which may be branched or unbranched.

8. A process according to claim 1 wherein the sulfur-containing organic compound is sulfolane.

9. A process according to claim 1 wherein the reaction produces trioxane and tetroxane.

10. A process according to claim 1 wherein during the process a reaction mixture includes the formaldehyde source, the sulfur-containing organic compound, and the catalyst, and wherein the reaction mixture comprises the sulfur-containing organic compound in an amount ranging from about 25 wt.-% to about 90 wt.-%.

11. A process according to claim 1, wherein the catalyst comprises trifluoromethanesulfonic acid, perchloric acid, methanesulfonic acid, toluenesulfonic acid, or sulfuric acid.

12. A process according to claim 1, wherein the formaldehyde source has a water content of less than about 20 wt.-%.

13. A process according to claim 1, wherein the formaldehyde source comprises an aqueous formaldehyde solution.

14. A process according to claim 13, wherein the aqueous formaldehyde solution contains formaldehyde in an amount from about 60 wt. % to about 90 wt. %.

15. A process according to claim 1, further comprising the step of separating the cyclic acetal from the liquid medium by distillation.

16. A process according to claim 1, further comprising the step of manufacturing polyoxymethylene from the cyclic acetal.

17. A process according to claim 1, wherein the formaldehyde source comprises gaseous formaldehyde.

18. A process for producing cyclic acetal comprising
   i) preparing a liquid reaction mixture comprising
      a) a formaldehyde source,
      b) an aprotic compound comprising a sulfur-containing organic compound and
      c) a catalyst, the catalyst comprising trifluoromethanesulfonic acid, perchloric acid, methanesulfonic acid, toluenesulfonic acid, sulfuric acid, or a solid acid ion-exchangepaterial; and
   ii) converting the formaldehyde source into cyclic acetals; wherein the cyclic acetals comprise trioxane.

19. A process according to claim 1, wherein the catalyst comprises a solid acid ion-exchange material.

20. A process according to claim 10, wherein the reaction mixture includes the formaldehyde source in an amount from about 20 wt. % to about 70 wt. %, contains the aprotic compound in an amount from about 25 wt. % to about 75 wt. %, and contains water in an amount less than about 20 wt. %.

21. A process according to claim 13, wherein during the process a reaction mixture comprises the formaldehyde source, the sulfur containing organic compound, and the catalyst and wherein the reaction mixture contains water in an amount less than about 20 wt. %.

22. A process for producing a cyclic acetal comprising:
   contacting a formaldehyde source with a liquid medium comprising a sulfur-containing organic compound in the presence of a catalyst, the sulfur-containing organic compound comprising an organic sulfoxide, a sulfone, or mixtures thereof; and
   at least partially converting the formaldehyde source into a cyclic acetal, wherein the cyclic acetal comprises trioxane.

23. A process as defined in claim 22, wherein the sulfur-containing organic compound comprises sulfolane.

* * * * *